(12) United States Patent  (10) Patent No.: US 6,629,998 B1
Lin  (45) Date of Patent: Oct. 7, 2003

(54) INTERVERTEBRAL RETRIEVAL DEVICE

(76) Inventor: Chih-I Lin, 14292 Spring Vista La., Chino Hills, CA (US) 91709

( * ) Notice: Subject to any disclaimer, the term of this patent is extended or adjusted under 35 U.S.C. 154(b) by 108 days.

(21) Appl. No.: 09/644,207

(22) Filed: Aug. 23, 2000

(51) Int. Cl.[7] .................................................. A61F 2/44
(52) U.S. Cl. ................................................... 623/17.11
(58) Field of Search ........................ 606/61; 623/17.16, 623/17.11, 17.15

(56) References Cited

U.S. PATENT DOCUMENTS

| 4,904,261 | A | * | 2/1990 | Dove et al. | 623/17.11 |
| 5,290,312 | A | * | 3/1994 | Kojimoto et al. | 623/17.11 |
| 5,405,391 | A | * | 4/1995 | Hednerson et al. | 606/61 |
| 5,425,772 | A | * | 6/1995 | Brantigan | 623/17.11 |
| 5,876,402 | A | * | 3/1999 | Errico et al. | 606/61 |
| 6,099,531 | A | * | 8/2000 | Bonutti | 623/17.11 |
| 6,231,610 | B1 | * | 5/2001 | Geisier | 623/17.11 |
| 6,235,034 | B1 | * | 5/2001 | Bray | 606/61 |
| 6,342,074 | B1 | * | 1/2002 | Simpson | 623/17.11 |

* cited by examiner

*Primary Examiner*—Todd E. Manahan
(74) *Attorney, Agent, or Firm*—Bacon & Thomas

(57) ABSTRACT

An intervertebral retrieval device comprising a filling body and one or more bone nails. The filling body is provided in one side thereof with one or more slanted holes to an upper contact surface and/or a lower contact surface of the filing body. The bone nails are inserted into the one or more slanted holes and fastened onto vertebrae contacting the upper contact surface and/or the lower contact surfaces from the external side of the filling body.

6 Claims, 5 Drawing Sheets

INTERVERTEBRAL RETRIEVAL DEVICE

FIELD OF THE INVENTION

The present invention relates to an intervertebral retrieval device which comprises a filling body and one or more bone nails.

BACKGROUND OF THE INVENTION

The conventional intervertebral disc spacer, for example, the RAMPS serial products made by AcroMed Corporation of the United States, is defective in design in that it does not become fused with the vertebrae, because endplates of vertebrae are not destroyed. The conventional intervertebral disc spacer is thus used in conjunction with the auxiliary fixation devices, such as the bone nail and the fixation rod, so as to prevent the disengagement of the disc spacer. The use of the auxiliary fixation devices refrain the intervertebral motion between the two vertebrae spaced by the disc spacer. In addition, the auxiliary fixation devices are not effective in averting the disengagement of the disc spacer with the vertebrae.

SUMMARY OF THE INVENTION

The objective of the present invention is to provide an intervertebral retrieval device.

It is another objective of the present invention to provide an intervertebral device comprising a filling body having a slanted hole, and A bone nail.

An intervertebral retrieving device constructed according to the present invention comprises:

a filling body provided in a side thereof with one or more slanted holes to an upper contact surface and/or a lower contact surface of said filling body; and one or more bone nails adapted to be received in said one or more slanted holes from said side with one ends of said one or more bone nails jutting out from said filling body, whereby said one or more bone nails penetrate from said upper contact surface and/or said lower contact surface of said filling body into vertebrae or their substituting bodies.

Preferably, said filling body has two slanted holes, and more preferably said two slanted holes include one slanted hole slanting upward to said upper contact surface and the other slanted hole slanting downward to said lower contact surface.

Preferably, said upper contact surface and/or said lower contact surface have a plurality of protruded teeth. More preferably, said plurality of protruded teeth are parallel lateral teeth.

Preferably, the device of the present invention further comprises an auxiliary fixation means at said side for preventing said one or more bone nails from detaching from said or more slanted holes. Said auxiliary fixation means may comprises recesses provided at said side and covers or a bar detent mounted in said recesses. In one of the preferred embodiments of the present invention, said recesses are C-shaped recesses, and said auxiliary fixation means is a U-shaped bar detent elastically received in C-shaped recesses and across said one or more slanted holes.

The bone nails of the present invention is locked into the vertebrae, which penetrate the filling body, so as to ensure that the filling body of the present invention does not slip out of the space between the vertebrae.

DETAILED DESCRIPTION OF THE INVENTION

Figure 1:
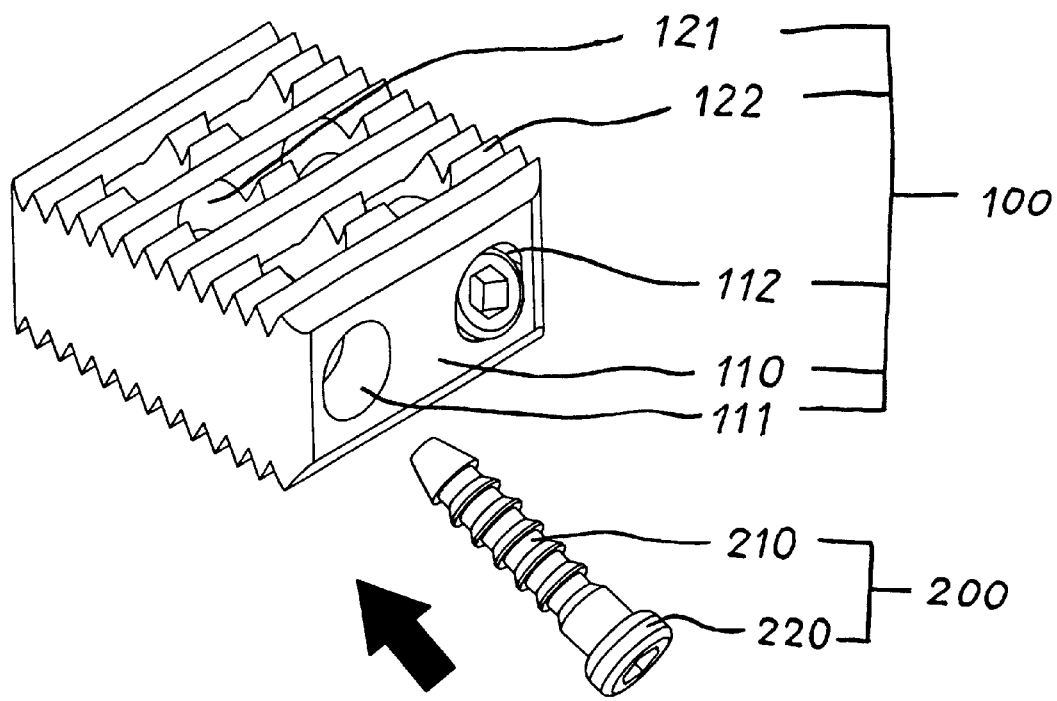
FIG. 1 shows a schematic view of a first preferred embodiment of the present invention, in which a bone nail is fastened.
Figure 2:
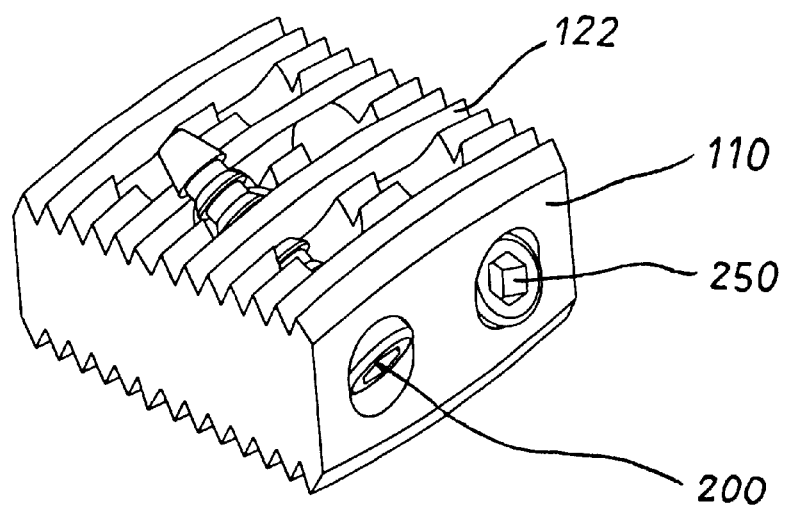
FIG. 2 shows a schematic view of the first preferred embodiment of the present invention, in which two bone nails are fastened.
Figure 3:
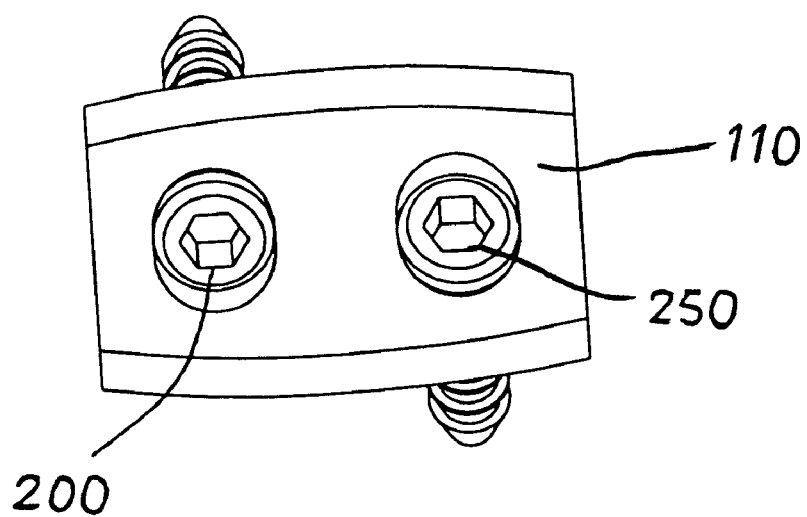
FIGS. 3 and 4 are side schematic view and front schematic view of the first preferred embodiment of present invention, in which two bone nails are fastened.
Figure 4:
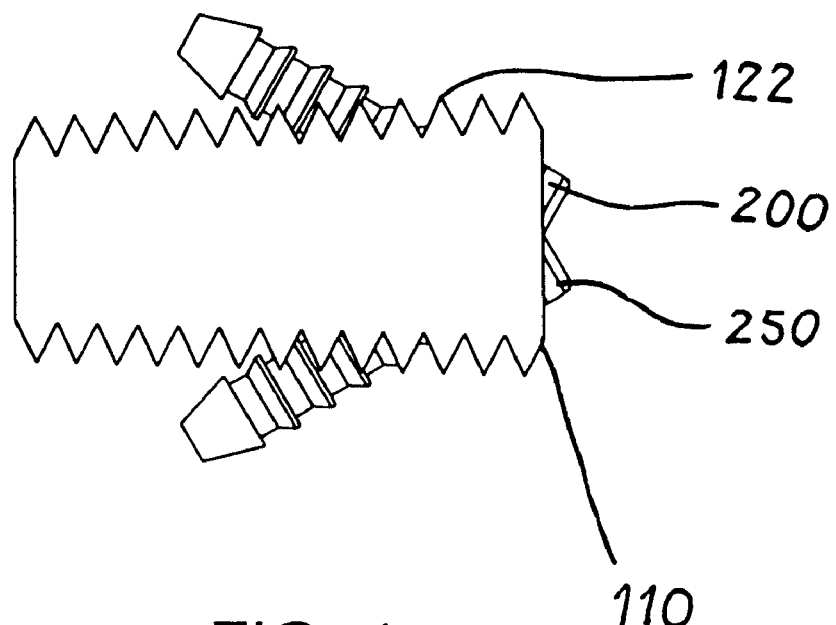

The present invention relates to an intervertebral retrieval device comprising a filling body, and one or more bone nails.

The filling body is provided in one side thereof with one or more slanted holes to an upper contact surface and/or a lower contact surface.

The bone nails are jutted out of the upper contact surface and/or lower contact surface via the slanted holes from the side of the filling body such that the bone nails are fastened onto the upper vertebra and/or lower vertebra, or their substitutes or similar devices.

The aforementioned "upper" refer to the direction toward the head after surgery. The word "lower" refers to the direction opposite to the "upper" direction. The so-called "side" refers to the side facing the incision and is preferably planar as illustrated in the drawings. The contact surfaces refer to the surfaces on which the endplates of the vertebrae come in contact.

The upper and/or lower contact surface of the filling body have protruded teeth, such as parallel lateral teeth, as shown in FIGS. 1–5, regular or random cones.

The upper contact surface and/or lower contact surface of the filling body are substantially planar or arcuate to be cooperative with the spinal cord.

The bone nails of the present invention may be conventional bone nails.

The bone nail may be fixedly received (such as threaded) in the slanted hole of the filling body. The bone nail may be inserted into the slanted hole of the filling body such that the bone nail is not substantially connected with the inner wall of the slanted hole of the filling body.

It is preferable that the bone nail is not fixedly received in the slanted hole of the filling body, so as to allow a greater micromotion between the filling body and the bone nail (the vertebrae), thereby promoting the bone ingrowth. In light of the bone nail being inserted slantingly into the slanted hole of the filling body, the filling body can be pulled out in the direction consistent with the inclination of the slanted hole of the filling body. However, the filling body is not allowed to move in this direction by the vertebra. In other words, the filling body will not slip out the bone nail, even though the bone nail and the slanted hole of the filling body are not substantially joined together.

The aforementioned filling body, bone nail, auxiliary fixation means may be any biologically compatible material for orthopedic surgery, such as stainless steel 316LVM, Ti-6-4, cobalt-molybdenum-nickel alloy, etc.

The present invention is further described by a preferred embodiment with reference to the accompanying drawings.

A first preferred embodiment of the present invention is shown in FIGS. 1–5, wherein a filling body 100 is provided on a side 110 thereof with two slanted holes 111 and 112, and protruded teeth 122 on an upper and lower contact surfaces. The slanted hole 111 has an outlet 121 on the upper contact surface, and the slanted hole 112 also has an outlet (not shown in the drawings) on the lower contact surface. Two bone nails 200 with each having a threaded portion 210 and a head 220 are received in the two slanted holes 111 and 112.

Figure 5:
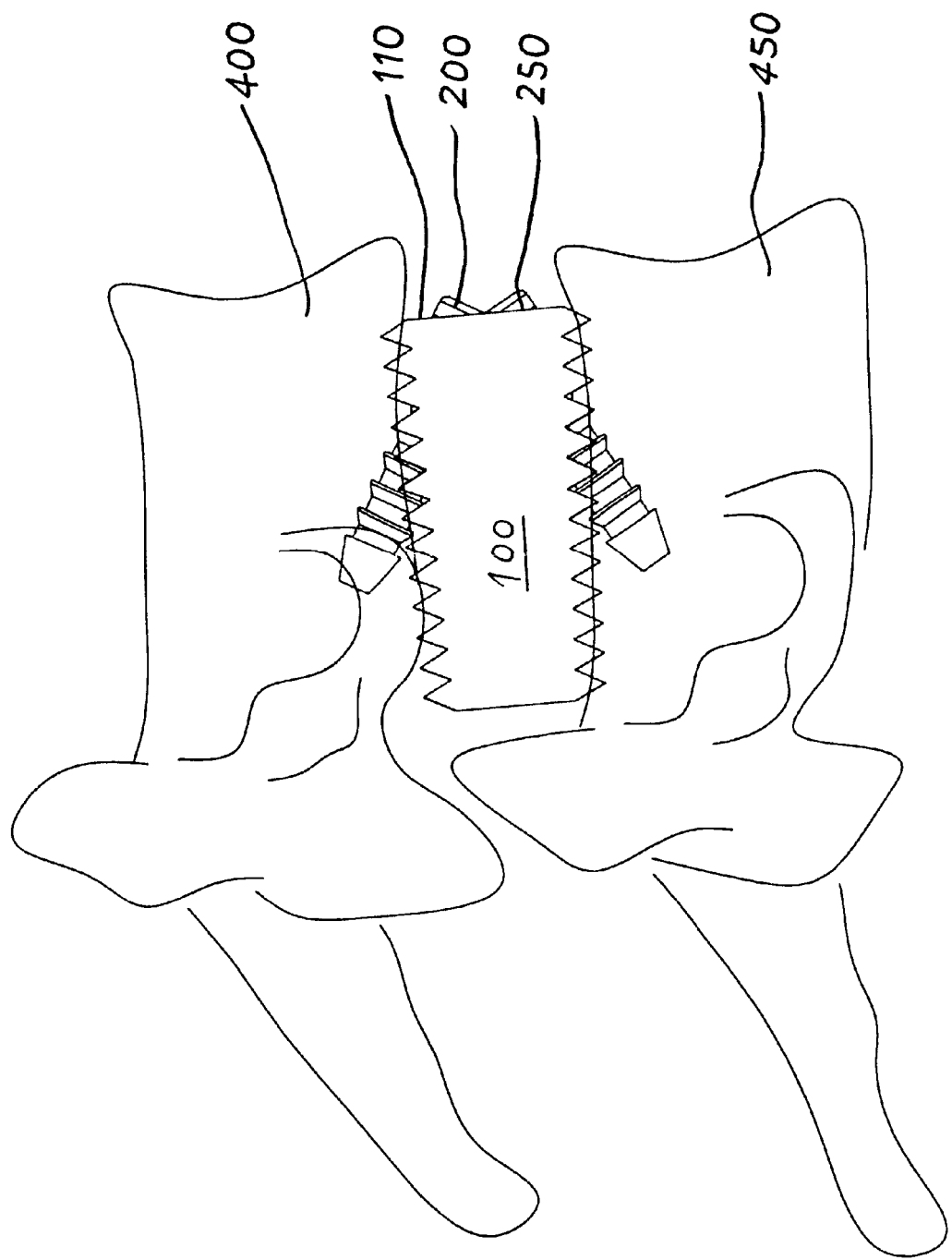
FIG. 5 is a side schematic view of the first preferred embodiment of present invention implanted between two vertebrae.

As shown in FIG. 5, the filling body 100 is implanted between two vertebrae 400 and 450, and the two bone nails 200 are then inserted into the two slanted holes from the side 110 and threaded into the two vertebrae 400 and 450.

Figure 6:
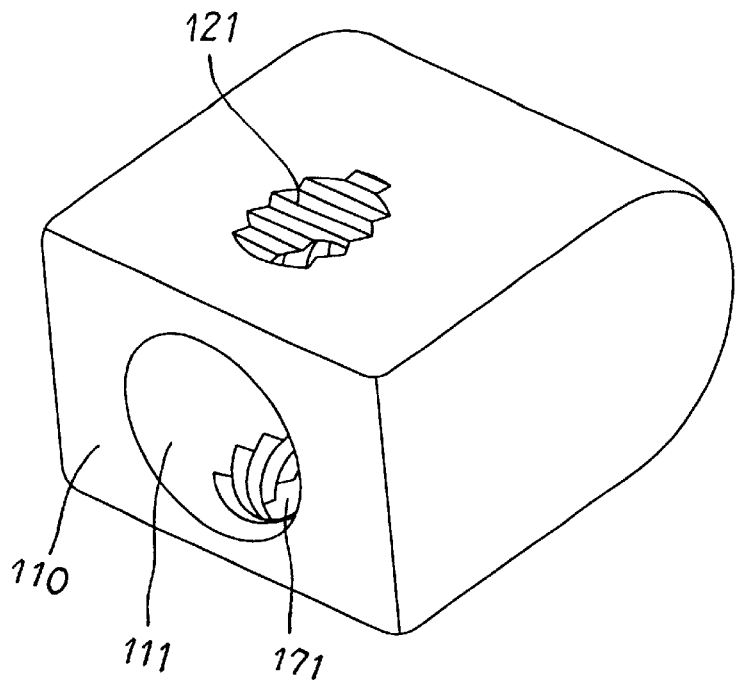
FIG. 6 is a schematic view of a filling body of a second preferred embodiment of the present invention.
Figure 7:
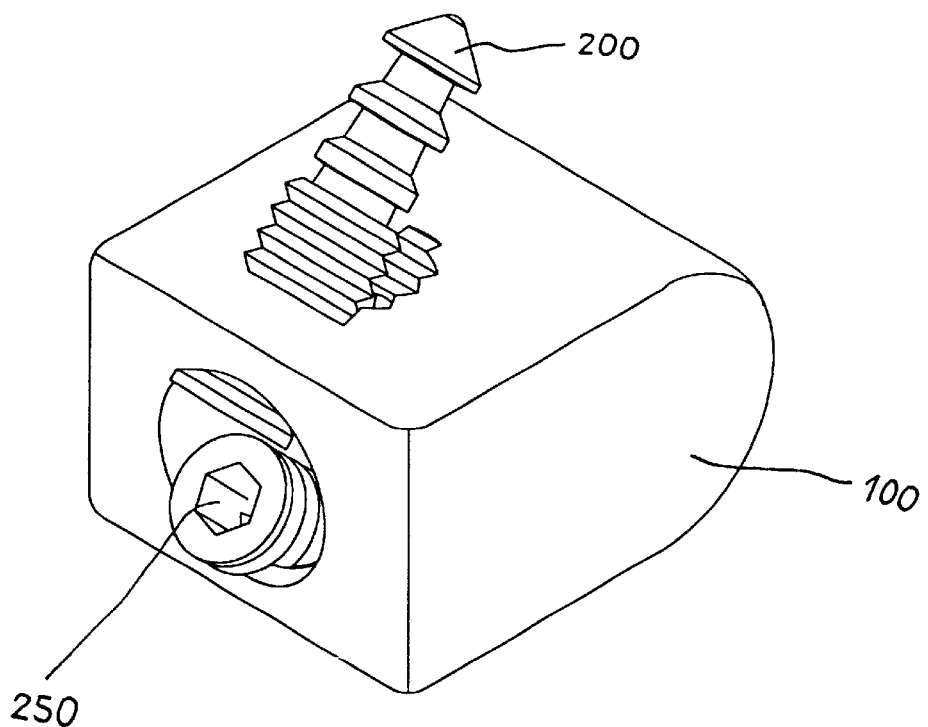
FIG. 7 is a schematic view of the second preferred embodiment of the present invention after the bone nail being fastened.

A second preferred embodiment of the present invention is shown in FIGS. 6 and 7, wherein a filling body 100 has only one hole 111 on one side 110 thereof. However, there are two slanted threaded holes 121' and 171 formed on the wall of the hole 111, with one being slanted to the upper surface, and with the other one being slanted to the lower contact surface. The contact surfaces of the filling body 100 are devoid of protuberance. Two bone nails 200 and 250 are threaded onto the two slanted threaded holes 121' and 171 as shown in FIG. 7.

Figure 8:
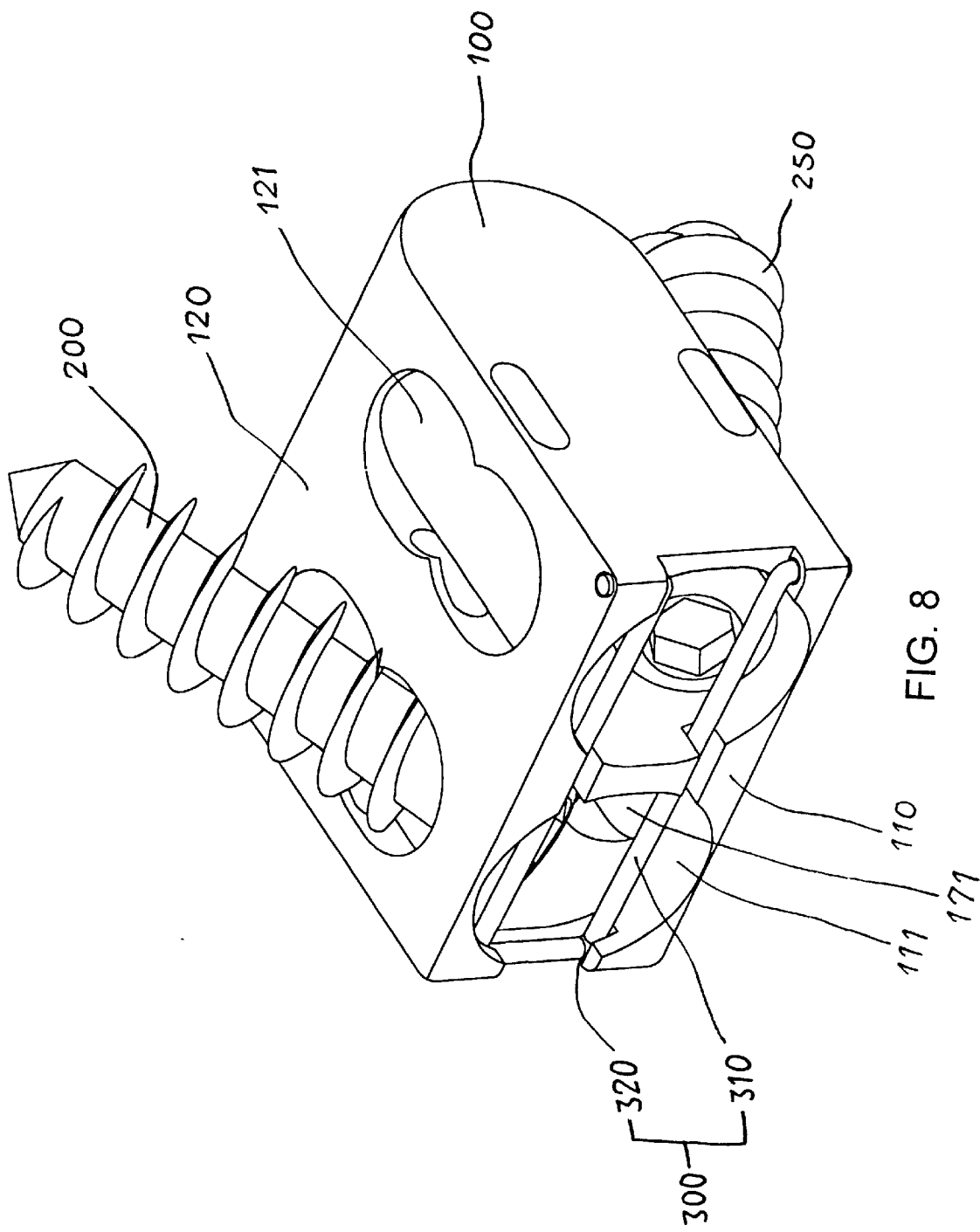
FIG. 8 shows a schematic view of a third preferred embodiment of the present invention.

A third preferred embodiment of the present invention similar to the second preferred embodiment shown in FIGS. 6 and 7 is shown in FIG. 8, wherein like elements and parts are designated with like numerals. In this embodiment, the filling body 100 contains two separate holes 111 on the side 110 with each having two slanted holes 121 and 171 formed on the wall thereof. The slant holes have an 8-shaped outlet on the contact surface. The third preferred embodiment of the present invention further comprises an auxiliary fixation means 300 including a U-shaped bar detent 310 pivotally mounted on one edge of the side 100 and C-shaped recesses 320 formed on the side 100 near the holes 111. Said U-shaped bar detent, is elastically received in said C-shaped recesses after the bone nails 200 and 250 being inserted into the slanted holes 121 and 171 and threaded into the vertebrae.

It can be seen from the various embodiments of the invention as illustrated in the figures that the intervertebral retrieving device of the present invention has the general shape depicted in the drawings which is non-wedge shaped.

What is claimed is:

1. A non wedge shaped intervertebral retrieving device comprising:

a filling body provided in a planar side thereof with two or more slanted holes to an upper contact surface and/or a lower contact surface of said filling body; and one or more bone nails adapted to be received in said one or more slanted holes from said planar side with one ends of said one or more bone nails jutting out from said filling body, whereby said one or more bone nails penetrate from said upper contact surface and/or said lower contact surface of said filling body into vertebrae or their substituting bodies; said upper contact surface and/or said lower contact surface having a plurality of protruded parallel lateral teeth.

2. The device as defined in claim 1, wherein said filling body has two slanted holes.

3. The device as defined in claim 2, wherein said two slanted holes include one slanted hole slanting upward to said upper contact surface and the other slanted hole slanting downward to said lower contact surface.

4. The device as defined in claim 1 further comprising an auxiliary fixation means at said planar side for preventing said two or more bone nails from detaching from said or more slanted holes.

5. The device as defined in claim 4, wherein said auxiliary fixation means comprises recesses provided at said planar side and covers or a bar detent mounted in said recesses.

6. The device as defined in claim 5, wherein said recesses are C-shaped recesses, and said auxiliary fixation means comprises a U-shaped bar detent elastically received in said C-shaped recesses and across said two or more slanted holes.

* * * * *